United States Patent
Nielsen et al.

(10) Patent No.: US 10,166,338 B2
(45) Date of Patent: Jan. 1, 2019

(54) DRUG DELIVERY SYSTEM AND DEVICE WITH CAP FUNCTION

(75) Inventors: Karsten Baker Nielsen, Copenhagen Oe (DK); Andre Larsen, Dragoer (DK)

(73) Assignee: Novo Nordisk A/S, Bagsvaerd (DK)

( * ) Notice: Subject to any disclaimer, the term of this patent is extended or adjusted under 35 U.S.C. 154(b) by 1903 days.

(21) Appl. No.: 13/496,671

(22) PCT Filed: Sep. 9, 2010

(86) PCT No.: PCT/EP2010/063246
§ 371 (c)(1),
(2), (4) Date: May 30, 2012

(87) PCT Pub. No.: WO2011/032883
PCT Pub. Date: Mar. 24, 2011

(65) Prior Publication Data
US 2012/0232474 A1    Sep. 13, 2012

Related U.S. Application Data (60) Provisional application No. 61/258,043, filed on Nov. 4, 2009.

(30) Foreign Application Priority Data

Sep. 21, 2009  (EP) ..................................... 09170841
Oct. 29, 2009  (EP) ..................................... 09174420

(51) Int. Cl.
*A61M 5/31*      (2006.01)
*A61M 5/24*      (2006.01)
(Continued)

(52) U.S. Cl.
CPC ............ *A61M 5/24* (2013.01); *A61M 5/3202* (2013.01); *A61M 5/3213* (2013.01);
(Continued)

(58) Field of Classification Search
CPC ...... A61M 2205/6045; A61M 2205/60; A61M 2005/2407; A61M 5/24; A61M 5/3213;
(Continued)

(56) References Cited

U.S. PATENT DOCUMENTS 4,883,049 A * 11/1989 McDonald ............... 128/202.22
5,213,483 A *  5/1993 Flaherty et al. ........... 417/477.2
(Continued)

FOREIGN PATENT DOCUMENTS

CN    101365505 A     2/2009
DE     20110690 U1    9/2001
(Continued)

OTHER PUBLICATIONS

Definition of "cap". Meriam-Webster Dictionary [Online]. http://www.merriam-webster.com/dictionary/cap. Accessed on Dec. 29, 2015.*

*Primary Examiner* — Jenna Zhang
(74) *Attorney, Agent, or Firm* — Wesley Nicolas (57) ABSTRACT

A system comprising first and second drug delivery devices (1) based on the same technology platform, each comprising a main portion (3) with a reservoir holding a type of drug, a drug outlet, and drug expelling means for expelling drug from the reservoir through the drug outlet, as well as a cap (100) releasably mountable to the main portion to enclose the drug outlet, each cap comprising a unique user-identifiable marking indicating the corresponding type of drug. The cap and main portion of each drug delivery device comprise a pair of corresponding key structures preventing the first cap from being mounted on the second main portion, and the second cap from being mounted on the first main portion.

10 Claims, 4 Drawing Sheets

(51) Int. Cl.
  *A61M 5/32* (2006.01)
  *A61M 5/315* (2006.01)

(52) U.S. Cl.
  CPC ..... *A61M 5/31551* (2013.01); *A61M 5/31585* (2013.01); *A61M 2005/2407* (2013.01); *A61M 2205/6045* (2013.01)

(58) Field of Classification Search
  CPC ............ A61M 5/3202; A61M 5/31551; A61M 5/31585
  See application file for complete search history.

(56) References Cited

U.S. PATENT DOCUMENTS

| | | | | |
|---|---|---|---|---|
| 5,293,913 | A | * | 3/1994 | Preszler ............... B41J 2/17523 141/100 |
| 5,530,531 | A | * | 6/1996 | Girard ................... B41J 2/1755 222/DIG. 1 |
| 5,569,026 | A | * | 10/1996 | Novak .................. A61M 5/142 417/477.1 |
| 5,740,794 | A | | 4/1998 | Smith et al. |
| 5,785,049 | A | | 7/1998 | Smith et al. |
| 5,954,700 | A | * | 9/1999 | Kovelman ........ A61M 5/31525 604/189 |
| 2006/0027233 | A1 | | 2/2006 | Zierenberg et al. |
| 2006/0100574 | A1 | * | 5/2006 | Izumi ..................... A61J 3/002 604/82 |
| 2008/0015519 | A1 | | 1/2008 | Klint et al. |
| 2010/0004603 | A1 | * | 1/2010 | Kristensen ............. A61M 5/24 604/207 |

FOREIGN PATENT DOCUMENTS

| | | | | |
|---|---|---|---|---|
| DE | 20110689 U1 | * | 1/2002 | ............ A61M 5/002 |
| DE | 10 2008 016987 A1 | | 10/2009 | |
| DE | 102008016987 A1 | * | 10/2009 | ........ A61M 5/31525 |
| EP | 2039384 | | 3/2009 | |
| JP | H01-179861 U | | 12/1989 | |
| JP | H01179861 | * | 12/1989 | |
| JP | H08730 A | | 1/1996 | |
| JP | H09168600 A | | 6/1997 | |
| JP | 2004538118 A | | 12/2004 | |
| WO | 9938554 | | 8/1999 | |
| WO | 03/086511 | | 10/2003 | |
| WO | WO 03086511 A1 | * | 10/2003 | .......... A61M 5/3129 |
| WO | 2004/069314 A1 | | 8/2004 | |
| WO | 2007/060156 | | 5/2007 | |
| WO | 2008/059063 | | 5/2008 | |
| WO | WO 2008059063 A1 | * | 5/2008 | ............... A61M 5/24 |

\* cited by examiner

DRUG DELIVERY SYSTEM AND DEVICE WITH CAP FUNCTION

CROSS-REFERENCE TO RELATED APPLICATIONS

This application is a 35 U.S.C. § 371 national stage application of International Patent Application PCT/EP2010/063246 (published as WO 2011/032883), filed Sep. 9, 2010, which claimed priority of European Patent Application 09170841.2, filed Sep. 21, 2009, and European Patent Application 09174420.1, filed Oct. 29, 2009; this application further claims priority under 35 U.S.C. § 119 of U.S. Provisional Application 61/258,043, filed. Nov. 4, 2009.

The present invention generally relates to medical delivery devices. In specific embodiments the invention relates to injection devices adapted for transcutaneous delivery of an amount of drug.

BACKGROUND OF THE INVENTION

In the disclosure of the present invention reference is mostly made to the treatment of diabetes by delivery of insulin-containing drugs, however, this is only an exemplary use of the present invention.

Drug injection devices (typically for subcutaneous delivery) have greatly improved the lives of patients who must self-administer drugs and biological agents. Drug injection devices may take many forms, including simple disposable devices that are little more than an ampoule with an injection means or they may be highly sophisticated electronically controlled instruments with numerous functions. Regardless of their form, they have proven to be great aids in assisting patients to self-administer injectable drugs and biological agents. They also greatly assist care givers in administering injectable medicines to those incapable of performing self-injections.

In particular pen-style injection devices have proven to provide an accurate, convenient, and often discrete, way to administer drugs and biological agents, such as insulin. Modern devices have become more sophisticated and often include diverse and robust functions, such as memories for remembering time and amount of last dose, as well as, in the case of insulin devices, blood glucose monitors. While pen-style injection devices are typically cylindrically shaped with a needle protruding from the most distal portion of one end of the device, some devices have other shapes with the needle no longer protruding from the most distal part of an end of the device, e.g. Innovo® and InnoLet® from Novo Nordisk A/S, Bagsvaerd, Denmark.

Typically, injection devices use a pre-filled cartridge containing the medication of interest, e.g. 1.5 or 3.0 ml of insulin or growth hormone. The cartridge is typically in the form of a generally cylindrical transparent ampoule with a needle pierceable septum at one end and an opposed piston designed to be moved by the dosing mechanism of the injection device. The injection devices generally are of two types: "Durable" devices and "disposable" devices. A durable device is designed to allow a user to replace one cartridge with another cartridge, typically a new cartridge in place of an empty cartridge. In contrast, a disposable device is provided with an integrated cartridge which cannot be replaced by the user; when the cartridge is empty the entire device is discarded. Most injection devices are provided with a releasable pen cap covering the cartridge and the needle mount portion (see below), this allowing the user to inspect the content of the cartridge by removing the cap.

Often injection devices are provided as a system or family of devices containing different types of drugs, e.g. as known from WO 2004/069314. This application discloses a system of substantially identical injection devices, each individual injection device comprising a housing accommodating an ampoule containing drug sufficient for a number of injections and a dose setting mechanism by which a predetermined dose size can be set, and wherein each of the plurality of injection devices has a different predetermined dose size. The difference in the predetermined dose sizes can in one embodiment be based on the drug in the devices having different strength.

People suffering from diabetes are often treated with multiple daily injections in a regimen comprising one or two daily injections of long acting insulin to cover the basal requirement supplemented by bolus injections of short or rapid acting insulin to cover requirements related to meals.

A user will therefore often require two different injection devices, one containing the long acting insulin and another containing the short or rapid acting insulin. Often these injection devices have different colour indications to inform the user of the kind of insulin contained in the injection device. For example, the FlexPen® system offered by Novo Nordisk comprises pens for long and short acting insulins as well as for mixed insulin, the bodies and caps being identical with colour markings on the main body to differentiate the two types of insulin. In the SoloStar® system offered by Sanofi-Aventis the pens for long and short acting insulins have differently coloured bodies as well as caps. In addition these injection devices can be provided with tactile means such as a mechanical coding informing the user of the kind of insulin contained in the injection device. DE U 201 10 689 discloses a pen-shaped injection device having a cap with a clip for holding the injection device e.g. in a pocket of a shirt. The injection device is contained in a cut-out in a box. The physical shape of the injection device is according to this reference designed such that the right injection device fits into the right box. This is according to the prior art done by having devices with different of length of the clip and boxes with a similar shaped cut-out. DE 201 10 690 discloses an injection device comprising a driver portion, a cartridge and a cartridge holder. The cartridge holder can be provided with a coded ring-shaped protecting member which allows only a specifically configured cartridge to be mounted in the cartridge holder.

Another technique for drug delivery is to use pulmonary delivery of an aerosolized pharmaceutical formulation so that the active drug within the dispersion can reach the more or less distal regions of the lung. This way of administration has been used extensively for e.g. local administration of drugs for treatment of respiratory deceases, e.g. asthma, but has also been proposed for the treatment of diabetes with insulin. A variety of aerosolization systems have been proposed to disperse pharmaceutical formulations. For example, U.S. Pat. No. 5,785,049 and U.S. Pat. No. 5,740,794, the disclosures of which are herein incorporated by reference, describe exemplary powder dispersion devices which utilize a compressed gas to aerosolize a powder. Other types of aerosolization systems include so-called MDI's (which typically have a drug that is stored in a propellant), nebulizers (which aerosolize liquids using compressed gas, usually air), and the like. Another technique is the use of inspired gases to disperse the pharmaceutical formulation. In this way, the patient is able to provide the energy needed to aerosolize the formulation by the patient's own inhalation.

Corresponding to the administration of two or more drugs using injection devices, it may also be necessary to use two or more inhalation devices.

Although the prior art discloses a number of solutions of how to differentiate similar or otherwise identical drug delivery devices containing different kinds of drugs, there is still a need for drug delivery devices which in a simple and effective manner provides a strong identification of the kind of drug contained in a specific device, this reducing the risk of a user inadvertently taking the incorrect kind of drug.

Having regard to the above, it is an object of the present invention to provide a system of drug delivery devices which in a simple and cost-effective manner reduces the likelihood of a user taking the wrong kind of drug.

DISCLOSURE OF THE INVENTION

In the disclosure of the present invention, embodiments and aspects will be described which will address one or more of the above objects or which will address objects apparent from the below disclosure as well as from the description of exemplary embodiments.

Thus, in accordance with a first aspect a system is provided comprising at least first and second drug delivery devices. The first drug delivery device comprises a first main portion comprising a first reservoir holding a first type of drug, a first drug outlet, and first drug expelling means (e.g. mechanical means operated by the user of by electric power or a pressurized propellant) for expelling drug from the first reservoir through the first drug outlet, as well as a first cap releasably mountable to the first main portion to enclose the first drug outlet, the first cap comprising a first user-identifiable marking (e.g. visual or tactile) indicating the first type of drug. The second drug delivery device comprises a second main portion comprising a second reservoir holding a second type of drug, a second drug outlet, and second drug expelling means for expelling drug from the second reservoir through the second drug outlet, as well as a second cap releasably mountable to the second main portion to enclose the second mount, the second cap comprising a second user-identifiable marking indicating the second type of drug. The cap and main portion of each drug delivery device comprise a pair of corresponding key structures preventing the first cap from being mounted on the second main portion, and the second cap from being mounted on the first main portion. Indeed, this feature would be the case for any two completely different devices, thus the drug delivery devices in the system of the present invention are based on the same technology platform.

"Technology platform" is meant to mean the basic structure upon which the injection devices in the system are based, e.g. the mechanism for setting and expelling a dose of fluid drug from a drug-filled cartridge. In order to be based on the same technology platform, the injection devices of the system must work by the same mechanical principles i.e. the individual constructional components of each injection device must be the same and interact in the same way. Technology platform products share underlying structures or basic architectures that are common across a group of products or that will be the basis of a series of products commercialized over a number of years. Several products may be derived from a common technology platform. Members of a product family normally have many common parts and assemblies. Thus, two drug delivery devices sharing the same technology platform may in accordance with the present invention have e.g. at least 50%, 75% or 90% interchangeable parts (excluding non-structural parts as e.g. labels). To be interchangeable the parts may be morphologically identical or they may be fully identical.

By providing a system in which a given device cap can only be mounted on a corresponding device main portion the cap can be used to safely identify the drug content of a given drug delivery device without the risk of a user mounting a given cap on a non-corresponding device main portion with the possible risk of taking the wrong medication, e.g. mounting a cap indicating short acting insulin on a main device portion containing long acting insulin. The different caps of the system may vary by e.g. colour and/or physical configuration.

As appears, the above-described coding feature provides a drug delivery system which is much safer in use than previous systems on the markets using e.g. colour marked caps, such caps being identical apart from the colour and thus allowing non-corresponding caps and main portions to be attached to each other with the resulting possible risk of taking the wrong medication.

The delivery system may comprise at least one further drug delivery device, each further device having a main portion and a cap comprising a pair of corresponding key structures, wherein the key structure of any given cap prevents the given cap to be mounted on a main portion of another drug delivery device of the system.

In exemplary embodiments the corresponding key structures are mechanical, e.g. "key hole" and "key" structures allowing only corresponding cap and main portions to be assembled. The key structure of each cap may be arranged interiorly in the cap, whereas each main portion of the system may comprise a reservoir holder enclosing at least a portion of a reservoir, the reservoir holder comprising the key structure of the main portion.

Alternatively the corresponding key structures may be electronic or electric, e.g. in case the cap and/or the main portion comprise electronic means, placing a non-corresponding cap on a given main portion would result in the cap and/or main portion producing an alarm, e.g. a visual, tactile or sound signal.

In exemplary embodiments the drug delivery devices are drug injection devices adapted to expel a liquid drug formulation from a reservoir, e.g. a cartridge comprising a displaceable piston. The means for displacing the piston and thereby expel drug may be in the form of a user settable and user actuated mechanism, e.g. as disclosed in U.S. Pat. No. 6,004,297 or US 2009/054839 which are hereby incorporated by reference.

In an exemplary embodiment each main portion comprises a mount for mounting a needle assembly in fluid communication with the reservoir, the corresponding cap being adapted to enclose the mount when mounted on the main portion. The system may correspondingly comprise one or more needle assemblies each comprising a hub adapted to be mounted on any of the mounts of the system, and a hollow needle mounted in the hub and comprising a distal pointed end and a proximal end, the proximal end being adapted to be arranged in fluid communication with a reservoir when the hub is mounted on a mount. When mounted on a corresponding main portion the caps of the system may be adapted to enclose a needle assembly mounted on the mount.

In a further exemplary embodiment each main portion comprises a mouthpiece, the corresponding cap being adapted to enclose the mouthpiece when mounted on the main portion.

To further improve handling and convenience the cap may be provided with one or more inspection openings or windows allowing a user to inspect at least a portion of a mounted needle assembly. In this way a user does not have to remove the cap to check if a needle assembly is mounted or to check the reservoir.

Correspondingly, the main portion may be provided with a user-inspectable portion adapted to be covered by the cap in a mounted position, the cap being provided with one or more inspection openings or windows allowing a user to inspect at least a portion of the user-inspectable portion when the cap is mounted on the main portion.

For example, the user-inspectable portion may comprise a transparent reservoir portion allowing a user to inspect drug contained in the reservoir or the position of a piston located in the reservoir. For easier inspection of the transparent reservoir the cap may be provided with a second set of inspection openings or windows arranged generally opposite the first set, this allowing light to travel through the reservoir.

The cap may be generally non-transparent and be provided with one or more transparent windows, the transparent windows comprising means for reducing transmission of light detrimental to drug contained in the reservoir, e.g. a UV filter. The cap may optionally be provided with the additional features described in co-pending applications PCT/EP2010/058322.

In the above described embodiments the main portion of the drug delivery device comprises a reservoir, however, in alternative versions the different embodiments may be adapted to receive a replaceable reservoir, e.g. a cartridge or canister to be used in combination with a durable type delivery device.

As used herein, the term "drug" is meant to encompass any drug-containing formulation capable of being administered to a patient in a controlled manner, e.g. passed through a delivery means such as a cannula or hollow needle, such as a liquid, solution, gel or fine suspension, or passed through a nozzle or mouthpiece as an aerosol or powder. Representative drugs include pharmaceuticals such as peptides (e.g. insulins, insulin containing drugs, GLP-1 containing drugs as well as derivates thereof), proteins, and hormones, biologically derived or active agents, hormonal and gene based agents, nutritional formulas and other substances in either solid (dispensed), powder or liquid form. In the description of the exemplary embodiments reference will be made to the use of insulin containing drugs or drugs having insulin-like effects. Correspondingly, the term "subcutaneous" infusion is meant to encompass any method of transcutaneous delivery to a subject.

BRIEF DESCRIPTION OF THE DRAWINGS

In the following the invention will be further described with reference to the drawings, wherein.

In the figures like structures are mainly identified by like reference numerals.

DESCRIPTION OF EXEMPLARY EMBODIMENTS

When in the following terms such as "upper" and "lower", "right" and "left", "horizontal" and "vertical" or similar relative expressions are used, these only refer to the appended figures and not to an actual situation of use. The shown figures are schematic representations for which reason the configuration of the different structures as well as there relative dimensions are intended to serve illustrative purposes only.

Figure 1:
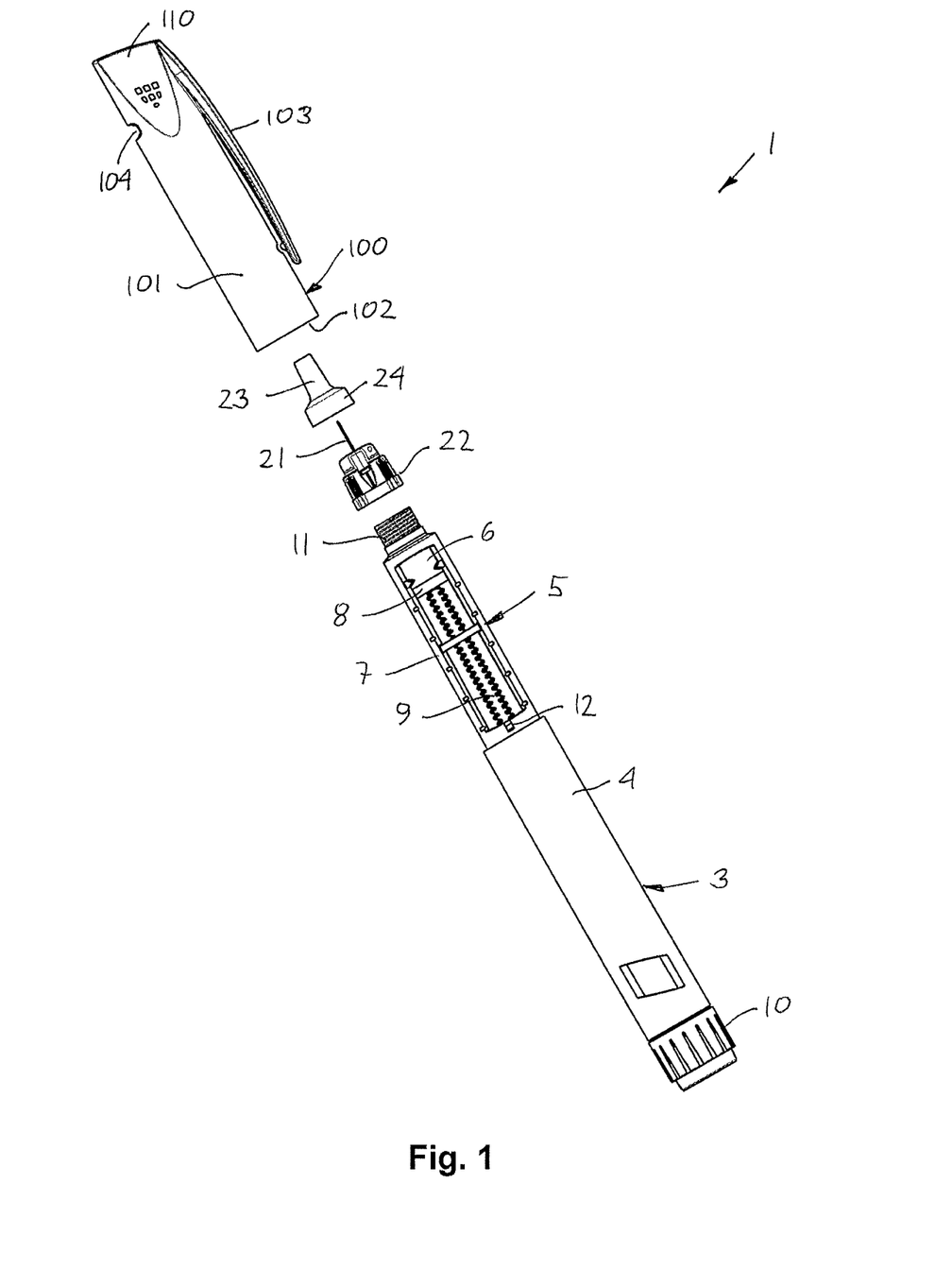
FIG. 1 shows a first embodiment of a drug delivery pen and a needle assembly.

Referring to FIG. 1 a pen-formed drug delivery device 1 will be described. The device corresponds to the general type of device to which the present invention relates but does not incorporate the present invention. The pen comprises a cap portion (or "pen cap") 100 and a main (or body) portion 3 having a proximal part 4 in which a drug expelling mechanism is arranged, and a distal reservoir part 5 in which a drug-filled transparent cartridge 6 with a distal needle-penetratable septum is arranged and hold in place by a cartridge holder 7 mounted to the proximal part, the cartridge holder having openings allowing a portion of the cartridge to be inspected. The cartridge is provided with a piston 8 driven by a piston rod 9 forming part of the expelling mechanism. A proximal-most button 10 serves to manually set and expel a desired dose of drug. This type of a pen-formed drug delivery device is well known, see e.g. WO 99/38554 to which reference is made for further details in respect of the internal construction of the shown type of pen. In the shown embodiment the pen is a disposable pre-filled device in which the cartridge holder is permanently attached to the proximal part of the main part, the cartridge holder being provided with distal coupling means in the form of an external thread 11 adapted to engage an inner thread of a needle assembly, see below. Alternatively the pen may be a "durable" device in which the cartridge holder is releasably attached to the main part, this allowing the piston rod to be pushed back and a new cartridge to be mounted. In such an arrangement the connection for the needle assembly may be part of the cartridge. The pen cap 100 made from a non-transparent material comprises a generally cylindrical sleeve 101 with a proximal closed end and a distal opening 102, a pocket clip 103 and an inspection opening 104. The proximal end is provided with two opposed generally planar gripping surfaces 110. Special features like e.g. the inspection opening and the gripping surfaces are not relevant for the present invention.

FIG. 1 further shows a needle assembly comprising a hollow infusion needle 21 mounted a cup-formed hub 22 with an inner coupling means in the form of a thread adapted to connect to the external thread 11 of the pen device. The needle comprises a distal pointed portion protruding from the hub as well as a proximal pointed portion adapted to penetrate the cartridge septum when the hub 22 is mounted on the thread 11. In an alternative embodiment a bayonet coupling may be used instead of the threaded connection, e.g. the cup may be provided with a plurality of inwardly projecting protrusions adapted to engage corresponding grooves formed distally on the pen device as disclosed in US 2008/0015519 and shown in FIG. 4. The needle assembly further comprises a needle cap 23 with a skirt portion 24 adapted to releasably engage the hub to thereby protect the distal end of the needle. The needle is normally provided sterile in a container (not shown) having an opening sealed by a peelable membrane, the container being in releasable, e.g. frictional, engagement with the needle hub. The pen-formed drug delivery device 1 and the needle assembly together form a system.

Figure 2:
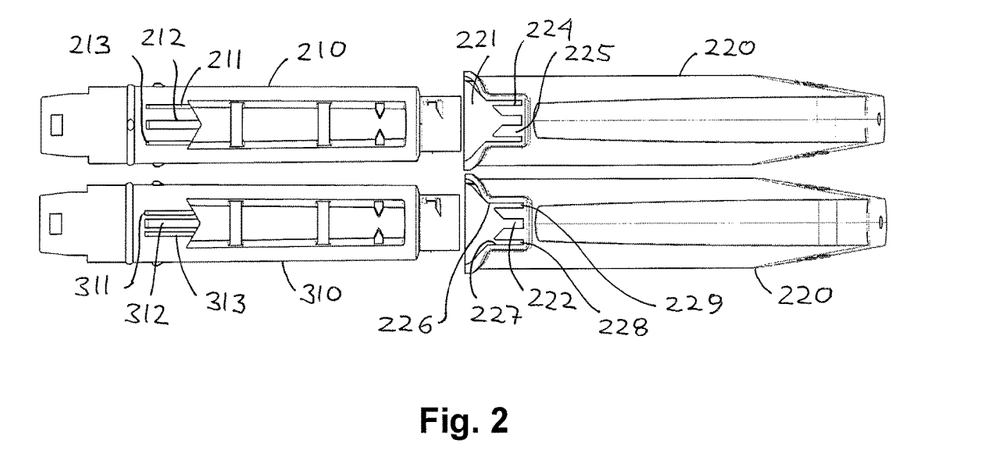
FIG. 2 shows two pairs of pen caps and cartridge holders corresponding to a first embodiment of the invention.
Figure 3:
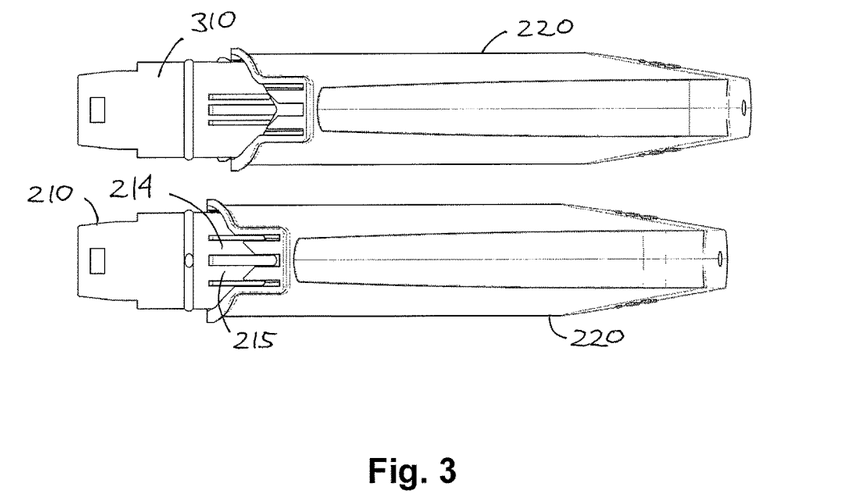
FIG. 3 shows match and mismatch of pen caps and cartridge holders of the first embodiment.

Turning to FIGS. 2 and 3 a first embodiment of the invention will be illustrated. FIG. 2 shows a pair of a first cartridge holder 210 and corresponding first pen cap 220 (in fact, two identical first caps are shown), the pen having a number of axially arranged ribs at the proximal end and the cap having a number of corresponding projections at its proximal end adapted to fit between the ribs. More specifically, the first cartridge holder is provided with three ribs in the form of a central wider rib 212 and two more narrow outer ribs on each side, thereby forming two cartridge slots 214, 215, the central rib protruding distally relative to the outer ribs. The cap comprises a proximal cut-out portion 221 with two opposed axially arranged edges 226, 227 between which two axially oriented projections 224, 225 are arranged, thereby forming a first central cap slot 222 between the two projections as well as second and third cap slots 228, 229 between each projection and its neighbouring edge. The proximal free end surfaces of the projections are inclined towards the central slot.

In accordance with the invention the specific combination of ribs 212, 211, 213 characterized by e.g. their number, width and spacing provide a "key hole" pattern into which a corresponding "key" pattern formed by the cap slots 222, 228, 229 will fit, this as illustrated by the lower matching pair of a cartridge holder and cap shown in FIG. 3. As also appears, the inclined surfaces of the on the cap projections help guide the central rib 212 into the gap between the projections.

FIG. 2 also shows a second cartridge holder 310 provided with a similar set of ribs 311, 312, 313 as on the first cartridge holder, however, the spacing between the ribs are different, this preventing the first cap to be mounted on the second cartridge as illustrated by the upper non-matching pair of cartridge holder and cap shown in FIG. 3. Indeed, a second cap (not shown) with a key corresponding to the second cartridge holder will be provided in a system in accordance with the invention, such a second cap having a combination of slots allowing it to be mounted on the second cap 310 but not on the first cap 210. Indeed, a system in accordance with the invention may comprise three or more matching pairs of a cartridge holder and pen cap, the spacing and width of the ribs and corresponding slots being unique for each such pair.

Figure 4:
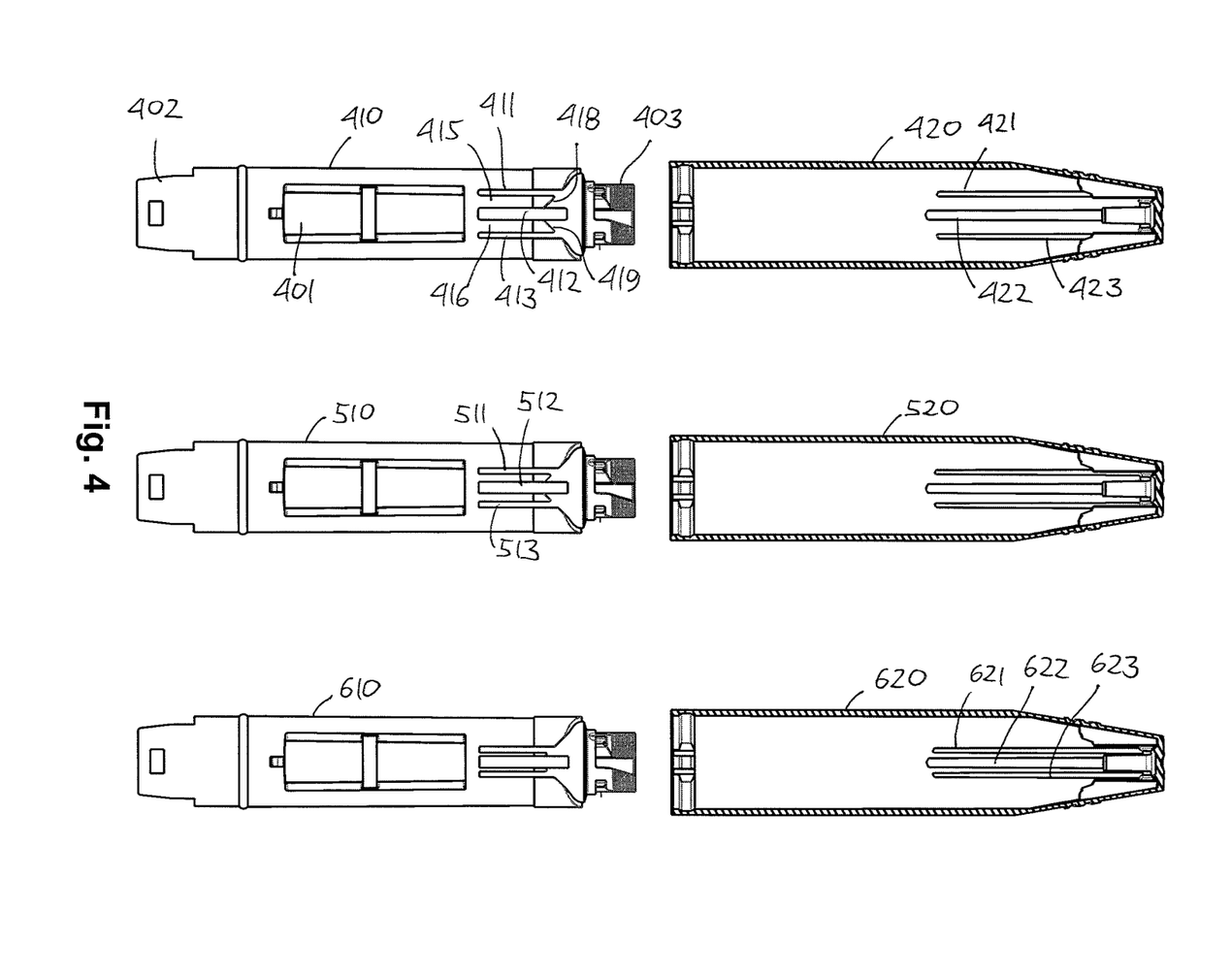
FIG. 4 shows three pairs of pen caps and cartridge holders corresponding to a second embodiment of the invention.
Figure 5:
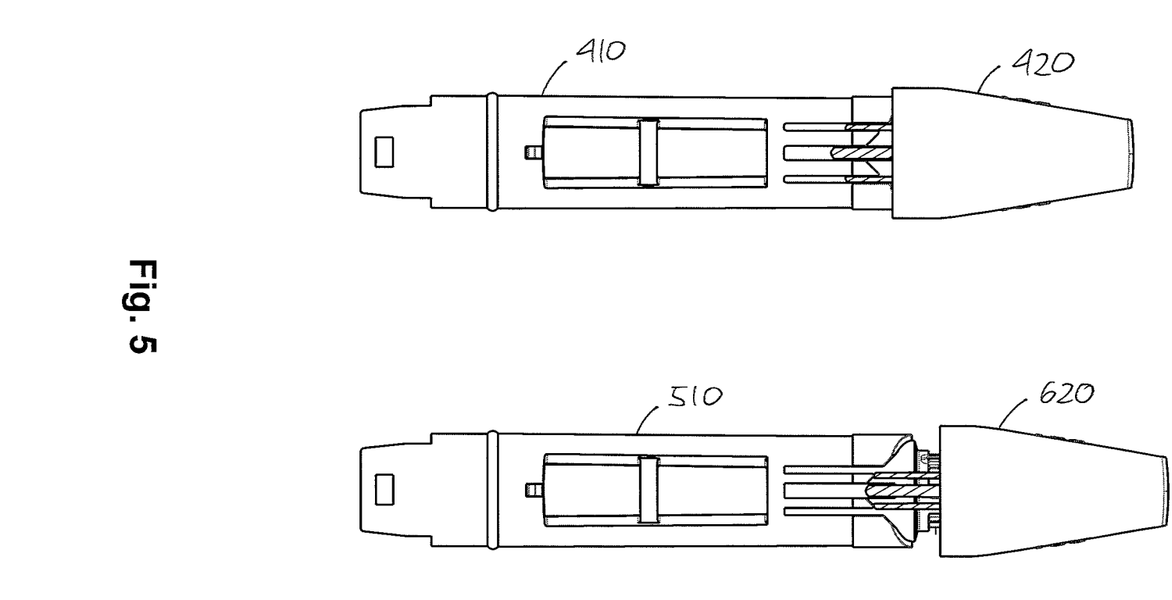
FIG. 5 shows match and mismatch of pen caps and cartridge holders of the second embodiment.

Turning to FIGS. 4 and 5 a second embodiment of the invention will be described. FIG. 4 shows in part a system 2 comprising a first pair of a first cartridge holder 410 and corresponding first pen cap 420, a second pair of a second cartridge holder 510 and corresponding second pen cap 520, and a third pair of a third cartridge holder 610 and corresponding third pen cap 620. The main portions of the drug delivery devices are represented only by the cartridge holders, however, the remaining part of each main portion may have the same general configuration as the drug delivery device shown and described with reference to FIG. 1. The cartridge holders and the pen caps have the same general configuration comprising a number of common features which will be described with reference to the first pair.

The cartridge holder 410 comprises a central portion adapted to hold a drug cartridge and being provided with a number of windows or openings 401 allowing a drug-filled transparent cartridge to be inspected by a user, a proximal portion 402 adapted to engage a pen body, and a distal portion 403 comprising a mount in the form of a bayonet coupling for a needle assembly.

Distally on the central portion two sets of 180 degrees opposed coding structures are arranged, each set providing a "key hole" into which a corresponding "key" of a pen cap will fit. More specifically, the cartridge holder coding structure comprises first, second and third axially oriented grooves 411, 412, 413 with a pair of axially oriented ribs 415, 416 arranged between the first and second respectively the second and third groove. In the shown embodiment the ribs are flush with the surrounding general surface of the cartridge holder. The distally facing free end surfaces 418, 419 of the ribs and the neighbouring cartridge holder are inclined towards the central second groove, thereby serving as a guide for the key structures on the cab, see below. In the shown embodiment the central groove also serves as a window to allow inspection of the cartridge.

The pen cap 420 in FIG. 4 is shown in a longitudinal cross-sectional view disclosing one of two pairs of 180 degrees opposed "key" coding structures arranged on the proximal inner surface of the pen cap, i.e. the shown key is adapted to engage the opposed hidden key hole structure on the cartridge holder 410. The coding structure comprises first, second and third axially oriented ribs 421, 422, 423 with a pair of axially oriented grooves 415, 416 arranged between the first and second respectively the second and third rib. In the shown embodiment the grooves are flush with the surrounding general inner surface of the pen cap. In an alternative embodiment the coding structures may be arranged proximally on the cartridge with the cap coding structures arranged in the vicinity of the cap opening.

The specific spacing and width of the ribs 421, 422, 423 corresponds to the spacing and width of the grooves 411, 412, 413 on the cartridge holder 410, this allowing the first pen cap 420 to be axially mounted on the first cartridge holder 410. This is illustrated in FIG. 5 showing the first cartridge holder and the first pen cap in fitting engagement. As appears, to illustrate the engagement the distal wall portion of the cap has been cut away leaving only the rig structures.

FIG. 5 also shows how the specific spacing of ribs 621, 622, 623 and grooves 511, 512, 513 prevents the third cap 620 to axially engage the second cartridge holder.

In a specific implementation of the second embodiment the three different cartridge holders could be permanently attached to three pen main bodies and used to hold three drug cartridges containing three different drugs, the three pen caps being provided in three different colours corresponding to the different drugs. As appears, the coding system of the invention would prevent a wrong cap to be mounted on a given cartridge holder, thereby reducing the risk that a user would grab and use a wrong pen comprising the wrong drug.

In an alternative embodiment a system comprising two or more inhalation devices is provided, each device comprising aerosol generating means, an outlet in the form of a mouthpiece and a protective cap adapted to be mounted on the mouthpiece, e.g. as known from U.S. Pat. No. 7,278,425 which is hereby incorporated by reference. In such a system the corresponding key structures may be arranged on the mouthpiece respectively the cap.

In the above description of the preferred embodiments, the different structures and means providing the described functionality for the different components have been described to a degree to which the concept of the present invention will be apparent to the skilled reader. The detailed construction and specification for the different components are considered the object of a normal design procedure performed by the skilled person along the lines set out in the present specification.

The invention claimed is:

1. A drug delivery system comprising two drug delivery devices,
the first drug delivery device comprising:
a first main portion (410) comprising:
a first reservoir holding a first type of drug,
a first drug outlet, and
a first drug expelling mechanism for expelling drug from the first reservoir through the first drug outlet,
a first cap (420) releasably mountable to the first main portion to enclose the first drug outlet, the first cap comprising a first user-identifiable marking indicating the first type of drug,
the second drug delivery device comprising:
a second main portion (510) comprising:
a second reservoir holding a second type of drug,
a second drug outlet, and
a second drug expelling mechanism for expelling drug from the second reservoir through the second drug outlet,
a second cap (520) releasably mountable to the second main portion to enclose the second outlet, the second cap comprising a second user-identifiable marking indicating the second type of drug,
wherein the cap and main portion of each drug delivery device comprise a pair of corresponding key structures (421, 422, 423, 411, 412, 413) preventing the first cap from being mounted on the second main portion, and the second cap from being mounted on the first main portion, and
wherein the two drug delivery devices in the system are based on the same technology platform by having at least 50% interchangeable parts.

2. A drug delivery system as in claim 1, wherein each main portion comprises a mount (11, 403) for mounting a needle assembly (21, 22) in fluid communication with each respective reservoir, the corresponding cap being adapted to enclose the mount when mounted on the main portion.

3. A drug delivery system as in claim 2, further comprising at least one needle assembly comprising:
a hub (22) adapted to be mounted on any of the mounts of the system, and
a hollow needle (21) mounted in the hub and comprising a distal pointed end and a proximal end, the proximal end being adapted to be arranged in fluid communication with each respective reservoir when the hub is mounted on the mount.

4. A drug delivery system as in claim 3, wherein each cap of the system when mounted on the corresponding main portion are adapted to enclose a needle assembly mounted on each respective mount.

5. A drug delivery system as in claim 1, wherein each main portion comprises a mouthpiece, the corresponding cap being adapted to enclose the mouthpiece when mounted on the main portion.

6. A drug delivery system as in claim 1, comprising at least one further drug delivery device (610), each of the at least one further drug delivery device having a main portion and a cap (620) comprising a pair of corresponding key structures, wherein the pair of corresponding key structures prevents a cap of one drug delivery device of the system from being mounted on a main portion of another drug delivery device of the system.

7. A drug delivery system as in claim 1, wherein the pair of corresponding key structures (421, 422, 423, 411, 412, 413) are mechanical.

8. A drug delivery system as in claim 7, wherein the corresponding key structure of each respective cap is arranged interiorly in the respective cap.

9. A drug delivery system as in claim 1, wherein each main portion of the system comprises a reservoir holder enclosing at least a portion of each respective reservoir, each reservoir holder comprising the corresponding key structure of the respective main portion.

10. A drug delivery system as in claim 1, wherein the pair of corresponding key structures are electric or electronic.

* * * * *